(12) United States Patent
Saito et al.

(10) Patent No.: US 9,782,059 B2
(45) Date of Patent: Oct. 10, 2017

(54) ENDOSCOPE SYSTEM

(71) Applicant: OLYMPUS CORPORATION, Tokyo (JP)

(72) Inventors: Takashi Saito, Tokyo (JP); Takehiko Ito, Hidaka (JP); Sachiko Asatori, Kokubunji (JP); Kyosuke Mizuno, Hino (JP); Tomoya Sato, Tokorozawa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/386,272

(22) Filed: Dec. 21, 2016

(65) Prior Publication Data

US 2017/0100018 A1    Apr. 13, 2017

Related U.S. Application Data

(63) Continuation of application No. PCT/JP2015/081618, filed on Nov. 10, 2015.

(30) Foreign Application Priority Data

Nov. 13, 2014 (JP) .................. 2014-230812

(51) Int. Cl.
*A61B 1/04* (2006.01)
*A61B 1/00* (2006.01)
*G02B 23/24* (2006.01)

(52) U.S. Cl.
CPC .............. *A61B 1/04* (2013.01); *A61B 1/00* (2013.01); *A61B 1/00009* (2013.01); *G02B 23/2484* (2013.01)

(58) Field of Classification Search
CPC .......... A61B 1/04; A61B 1/00; A61B 1/00009
See application file for complete search history.

(56) References Cited

U.S. PATENT DOCUMENTS

2007/0088193 A1    4/2007 Omori et al.
2009/0244271 A1*  10/2009 Abe .................. A61B 1/00009
                                                                  348/65
2010/0331624 A1   12/2010 Suzuki et al.

FOREIGN PATENT DOCUMENTS

EP    1752083 A1    2/2007
EP    2335560 A1    6/2011
(Continued)

OTHER PUBLICATIONS

International Search Report dated Jan. 26, 2016 issued in PCT/JP2015/081618.

*Primary Examiner* — Nam Pham
(74) *Attorney, Agent, or Firm* — Scully, Scott, Murphy & Presser, P.C.

(57) ABSTRACT

An endoscope system includes: a signal processing apparatus that performs processing on an output signal outputted from an endoscope; a detecting section configured to detect a type of the endoscope; a function setting section configured to set a plurality of functions in the endoscope system; an input section configured to input data to the function setting section; an output section configured to output a list of setting states of the plurality of functions to a display section; and a storing section configured to store recommended setting data corresponding to the plurality of functions, wherein the function setting section sets the signal processing apparatus to selected one of the setting corresponding to the type of the endoscope and a setting recommended by the recommended setting data, according to an input from the input section, and sets the plurality of functions according to the type of the endoscope.

12 Claims, 13 Drawing Sheets

(56) References Cited

FOREIGN PATENT DOCUMENTS

| | | |
|---|---|---|
| JP | H06-125871 A | 5/1994 |
| JP | H08-123518 A | 5/1996 |
| JP | 2003-265410 A | 9/2003 |
| JP | 2003-334163 A | 11/2003 |
| JP | 2004-181231 A | 7/2004 |
| JP | 2005-000454 A | 1/2005 |
| JP | 2006-075239 A | 3/2006 |
| JP | 2007-313132 A | 12/2007 |
| JP | 4732548 B2 | 7/2011 |
| JP | 2013-009908 A | 1/2013 |
| WO | WO 2005/112737 A1 | 12/2005 |
| WO | WO 2010/044432 A1 | 4/2010 |

\* cited by examiner

FIG. 3

2A, 2B ⋯ {
GIF (UPPER DIGESTIVE TRACT ENDOSCOPE)
CF (LOWER DIGESTIVE TRACT ENDOSCOPE)
TJF (ENDOSCOPE FOR DUODENUM)
BF (ENDOSCOPE FOR BRONCHUS (RESPIRATORY ORGAN))
ENT (ENDOSCOPE FOR OTORHINOLOGY)
CYF (ENDOSCOPE FOR URINARY ORGAN)

FIG. 4

| SELECTIVE FUNCTION | SETTING A | SETTING B | SETTING C |
|---|---|---|---|
| OBSERVATION MODE | WLI | NBI | AFI |
| NOISE REDUCTION | OFF | LEVEL 1 TO 8 | |
| PRE-FREEZE | OFF | LEVEL 1 TO 8 | |
| COLOR MODE | MODE 1 | MODE 2 | MODE 3 |
| ZOOM | 1.0 | 1.2 | 1.4 |
| STRUCTURE EMPHASIS | A/B/E | 1~8 | |
| MASK SIZE | SMALL | MEDIUM (NORMAL) | LARGE |
| LIGHT ADJUSTMENT | 1~8 | | |
| PHOTOMETRY | Peak | Ave | Auto |
| LUMINANCE CONTROL | OFF | ON | |
| LIGHT AMOUNT | -8~+8 | | |
| SERVER COOPERATION | OFF | ON | |
| PERIPHERAL APPARATUS CONTROL | OFF | ON | |

FIG. 5

| SETTING MODE | | OVERVIEW OF FUNCTION |
|---|---|---|
| (ENDOSCOPE) TYPE MODE | GIF | SET WHEN UPPER DIGESTIVE TRACT ENDOSCOPE IS USED. |
| | CF | SET WHEN LOWER DIGESTIVE TRACT ENDOSCOPE IS USED. |
| | TJF | SET WHEN ENDOSCOPE FOR DUODENUM IS USED. |
| | BF | SET WHEN ENDOSCOPE FOR RESPIRATORY ORGAN IS USED. |
| | ENT | SET WHEN ENDOSCOPE FOR OTORHINOLOGY IS USED. |
| | CYF | SET WHEN ENDOSCOPE FOR URINARY ORGAN IS USED. |
| BLOOD VESSEL DETECTION | | MODE FOR DETECTING BLOOD VESSEL. USED IN INCREASING CONTRAST OF BLOOD VESSEL TO MORE CLEARLY DISPLAY BLOOD VESSEL. |
| GI/SP COORDINATION | | USED WHEN ENDOSCOPE FOR SURGERY AND ENDOSCOPE FOR DIGESTIVE ORGAN ARE SIMULTANEOUSLY USED. |
| WIDE AREA | | USED WHEN IT IS DESIRED TO DISPLAY ENDOSCOPIC IMAGE ON SCREEN IN LARGE SIZE. EFFECTIVE WHEN IT IS DESIRED TO VIEW ENDOSCOPIC IMAGE IN WIDE AREA. |
| RELEASE | | USED WHEN STILL IMAGE IS SAVED. USED IN A BROAD CASE WHEN IT IS DESIRED TO SAVE IMAGE WITH LESS BLUR. |
| SCREENING | | USED WHEN IT IS DESIRED TO CARRY OUT EXAMINATION IN SHORT TIME. |
| ESOPHAGUS | | USED WHEN IT IS DESIRED TO MAINLY PERFORM OBSERVATION OF ESOPHAGUS. |

FIG. 6

| SELECTIVE FUNCTION | GIF MODE | TJF MODE | ... | BLOOD VESSEL DETECTION | ... |
|---|---|---|---|---|---|
| OBSERVATION MODE | WLI | WLI | ... | NBI | ... |
| NOISE REDUCTION | LEVEL 2 | LEVEL 2 | ... | LEVEL 3 | ... |
| PRE-FREEZE | LEVEL 6 | LEVEL 6 | ... | LEVEL 3 | ... |
| COLOR MODE | MODE 1 | MODE 3 | ... | MODE 1 | ... |
| ZOOM | 1.0 | 1.2 | ... | 1.4 | ... |
| STRUCTURE EMPHASIS | A7 | A7 | ... | B8 | ... |
| MASK SIZE | LARGE | LARGE | ... | LARGE | ... |
| LIGHT ADJUSTMENT | 1 | 1 | ... | 5 | ... |
| PHOTOMETRY | Auto | Ave | ... | Auto | ... |
| LUMINANCE CONTROL | OFF | ON | ... | OFF | ... |
| LIGHT AMOUNT | 0 | +2 | ... | +2 | ... |
| SERVER COOPERATION | ON | ON | ... | OFF | ... |
| PERIPHERAL APPARATUS CONTROL | ON | ON | ... | ON | ... |

TYPE MODE

FIG. 7

| FUNCTION MENU | |
|---|---|
| VIDEO RELATED FUNCTION | OBSERVATION MODE FUNCTION |
| NOISE REDUCTION<br>PRE-FREEZE<br>COLOR MODE<br>ZOOM<br>STRUCTURE EMPHASIS<br>MASK SIZE<br>LIGHT ADJUSTMENT<br>PHOTOMETRY<br>LUMINANCE CONTROL | WLI MODE<br>NBI MODE<br>AFI MODE |
| | OBSERVATION PART RELATED FUNCTION |
| ILLUMINATION RELATED FUNCTION | OTORHINOLOGY<br>UROLOGY<br>UPPER DIGESTIVE TRACT<br>LOWER DIGESTIVE TRACT<br>BILE/PANCREATIC DUCTS<br>BRONCHUS (RESPIRATORY ORGAN) |
| LIGHT AMOUNT | |
| PERIPHERAL APPARATUS RELATED FUNCTION | |
| SERVER COOPERATION<br>PERIPHERAL APPARATUS CONTROL | |

FIG. 9

| USER NAME | USER A | — | — |
|---|---|---|---|
| SELECTIVE FUNCTION | GIF MODE | GIF MODE | TJF MODE |
| OBSERVATION MODE | WLI | WLI | WLI |
| NOISE REDUCTION | LEVEL 3 | LEVEL 2 | LEVEL 2 |
| ... | ... | ... | ... |

FIG. 10

| USER NAME | USER A | USER A | USER B | — |
|---|---|---|---|---|
| TYPE OF VP | D | E | D | D |
| SELECTIVE FUNCTION | GIF MODE | GIF MODE | GIF MODE | GIF MODE |
| OBSERVATION MODE | WLI | WLI | WLI | WLI |
| NOISE REDUCTION | LEVEL 3 | LEVEL 2 | LEVEL 2 | LEVEL 2 |
| PRE-FREEZE | LEVEL 6 | — | LEVEL 5 | LEVEL 6 |
| ... | ... | ... | ... | ... |

FIG. 15

| USER NAME | USER A | USER A | USER A | USER B | |
|---|---|---|---|---|---|
| TYPE OF VP | D | D | E | D | |
| TYPE OF LIGHT SOURCE DEVICE | G | H | G | G | |
| SELECTIVE FUNCTION | GIF MODE | GIF MODE | GIF MODE | GIF MODE | |
| OBSERVATION MODE | WLI | WLI | WLI | WLI | |
| NOISE REDUCTION | LEVEL 3 | LEVEL 3 | LEVEL 2 | LEVEL 2 | |
| ... | ... | ... | ... | ... | |
| LIGHT AMOUNT | 0 | +1 | 0 | 0 | |
| | | | | | |

FIG. 16

| | |
|---|---|
| MONITOR | HD-SDI OUTPUT SETTING |
| | ASPECT RATIO 16:9 |
| VTR | HD-SDI RECORDING STATE |
| PRINTER | OPERATION ON |
| NETWORK | CONNECTION STATE |

FIG. 17

MONITOR    SDI OUTPUT

3G-SDI (RECOMMENDED)

HD-SDI

SD-SDI (SETTING IMPOSSIBLE)

ASPECT RATIO

16:9 (RECOMMENDED)

5:4

4:3 (SETTING IMPOSSIBLE)

FIG. 18

MENU SCREEN

SETTING ITEM F1

\*\*\*\*

SETTING ITEM F2

\*\*\*\*

⋮

ENDOSCOPE SYSTEM

CROSS REFERENCE TO RELATED APPLICATION

This application is a continuation application of PCT/JP2015/081618 filed on Nov. 10, 2015 and claims benefit of Japanese Application No. 2014-230812 filed in Japan on Nov. 13, 2014, the entire contents of which are incorporated herein by this reference.

BACKGROUND OF THE INVENTION

1. Field of the Invention

The present invention relates to an endoscope system that performs observation in setting corresponding to a type of an endoscope actually in use.

2. Description of the Related Art

In recent years, endoscopes have been widely used in a medical field and the like. As endoscopes, different types of endoscopes are prepared according to observation parts. The endoscopes suitable for the observation parts make it easy to perform observation or inspection, treatment performed using a treatment instrument, and the like.

When the different types of endoscopes are connected to a common signal processing apparatus or a common light source apparatus, appropriate setting states are required according to the types of the endoscopes.

For example, Japanese Patent Application Laid-Open Publication No. H8-123518 serving as a first conventional example discloses that a control apparatus, to which a plurality of controlled apparatuses such as a light source apparatus are electrically connected via communication means, remotely controls the controlled apparatuses. The first conventional example also discloses that the control apparatus is connected to a central operation panel as well and a display section of the central operation panel displays operation switches, setting values, measured values, and the like of the controlled apparatuses.

Japanese Patent Application Laid-Open Publication No. 2005-454 serving as a second conventional example discloses that, by mounting a peripheral apparatus extension control board in an image processing apparatus to which an endoscope is connected, information such as apparatus names, function names, and setting values of a pneumoperitoneum instrument and an electronic knife apparatus functioning as peripheral apparatuses are displayed. The second conventional example also discloses that the peripheral apparatuses can be controlled on the basis of a peripheral apparatus control screen.

Japanese Patent Application Laid-Open Publication No. 2003-334163 serving as a third conventional example discloses an image processing apparatus that detects a type of an endoscope or a type of an image pickup device and displays an image subjected to predetermined image processing in an appropriate region even when the number of pixels of the image pickup device changes according to the detected type.

SUMMARY OF THE INVENTION

An endoscope system according to an aspect of the present invention includes: a signal processing apparatus to which one endoscope among a plurality of types of endoscopes is connected, the signal processing apparatus performing video processing for an output signal of an image pickup device mounted on the connected endoscope; an endoscope-type detecting section configured to detect a type of the endoscope connected to the signal processing apparatus; a function setting section configured to set a plurality of functions in the endoscope system including the signal processing apparatus, the endoscope connected to the signal processing apparatus, and one or more peripheral apparatuses connected to the signal processing apparatus; an input section configured to input, to the function setting section, data including an instruction for changing the setting; an output section configured to output, to a display section, a list of setting states of the plurality of functions set by the function setting section; and a recommended-setting-data storing section configured to store, in association with a name of an observation part or a medical department, recommended setting data for setting the plurality of functions respectively to recommended appropriate setting states, wherein the function setting section sets the signal processing apparatus to a selected one of the setting of the setting states corresponding to the type of the endoscope and a setting recommended by the recommended setting data, according to an input of the name of the observation part or the medical department inputted from the input section, and automatically sets the plurality of functions respectively to appropriate setting states according to the type of the endoscope detected by the endoscope-type detecting section.

BRIEF DESCRIPTION OF THE DRAWINGS

FIG. 3 is a diagram showing a plurality of types of endoscopes used in the first embodiment;

FIG. 4 is a diagram showing, in a table format, selective functions that can be selectively set in the embodiment;

FIG. 5 is a diagram showing, in a table format, setting modes such as an endoscope type mode for setting the selective functions;

FIG. 6 is a diagram showing, in a table format, an example in which selective functions are appropriately set according to a type and the like of a specific endoscope;

FIG. 7 is a diagram showing contents of a function menu for displaying functions that can be set in the embodiment;

FIG. 9 is a diagram showing a portion of, in a table format, an example in which the selective functions are further set according to user names besides the example in which the selective functions are set as shown in FIG. 6;

FIG. 10 is a diagram showing, in a table format, a part of setting data stored in a nonvolatile memory of an endoscope;

FIG. 15 is a diagram showing, in a table format, a part of setting data for setting the plurality of functions of the endoscope system to the appropriate setting states according to a type of a video processor configuring the endoscope system and a type of a light source apparatus functioning as a peripheral apparatus;

FIG. 16 is a diagram showing setting contents of a monitor functioning as a peripheral apparatus;

FIG. 17 is a diagram of display of details of recommended setting items and setting items that cannot be set in the case in which setting items in the monitor are changed; and FIG. 18 is an explanatory diagram of a state in which setting items that need to be set are picked up and displayed on a menu setting screen when a peripheral apparatus is designated.

DETAILED DESCRIPTION OF THE PREFERRED EMBODIMENT(S)

Embodiments of the present invention are explained below with reference to the drawings.

First Embodiment

Figure 1:
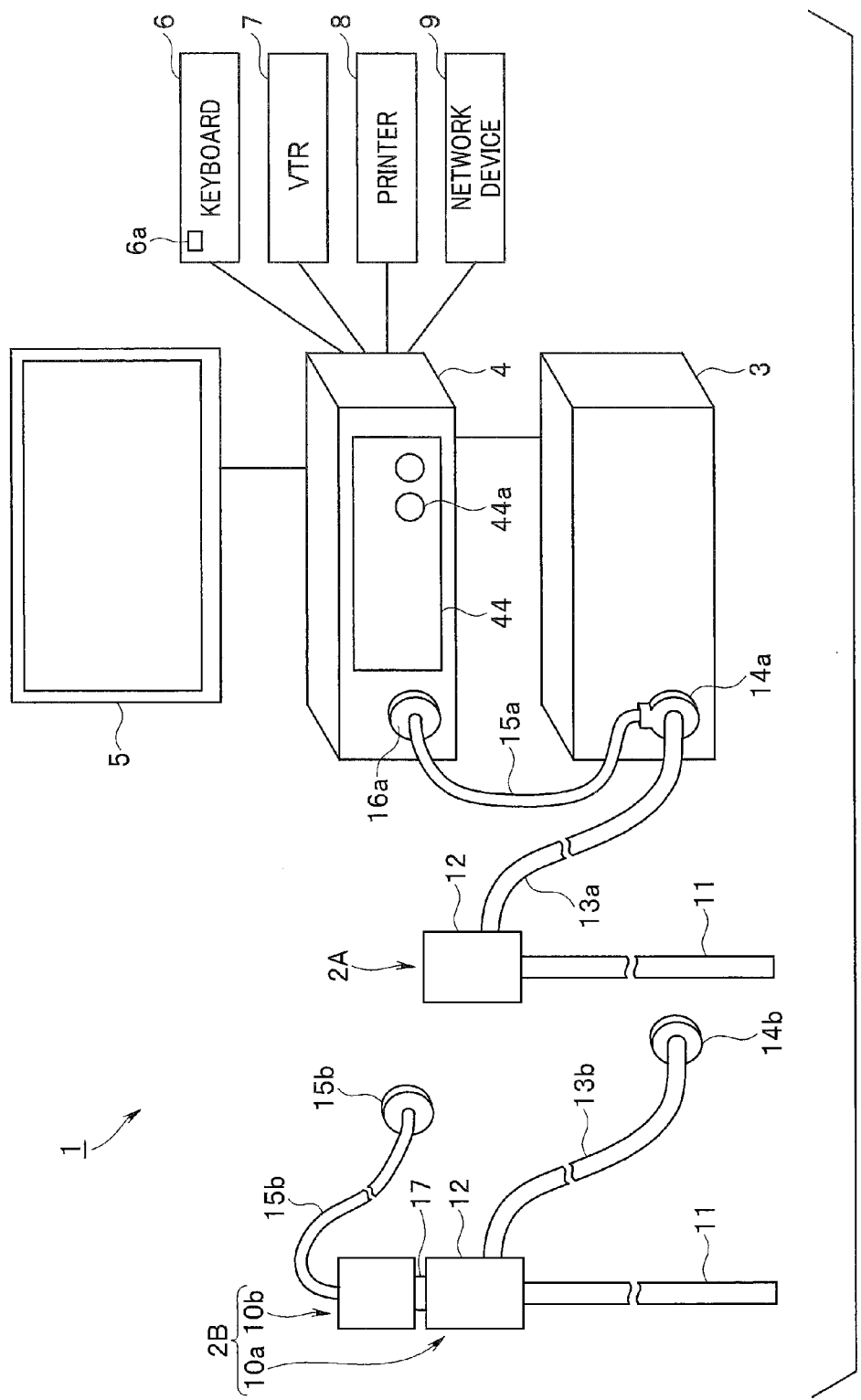
FIG. 1 is a diagram showing an overall configuration of an endoscope system in a first embodiment of the present invention.

As shown in FIG. 1, an endoscope system 1 in a first embodiment of the present invention includes endoscopes 2A, 2B, . . . (in FIGS. 1 and 2, only 2A and 2B are shown) inserted into a body of a patient, a light source apparatus 3 that supplies illumination light to an endoscope 2I (I=A, B, . . . ) connected to the light source apparatus 3, a video processor 4 forming a signal processing apparatus that performs signal processing for an image pickup device mounted on the connected endoscope 2I, a monitor 5 functioning as a display apparatus that displays a video signal (an image signal) generated by the video processor 4, a keyboard 6 connected to the video processor 4 and forming an input section, a VTR 7 functioning as a recording apparatus, a printer 8, and a network apparatus 9. Note that, in the present embodiment, the light source apparatus 3, the monitor 5, the VTR 7, the printer 8, and the network apparatus 9 form a plurality of peripheral apparatuses connected to the video processor 4 forming the signal processing apparatus.

The endoscope 2A includes an elongated insertion section 11, an operation section 12 provided at a proximal end (a rear end) of the insertion section 11, and a cable 13a extended from the operation section 12. A connector 14a at an end portion of the cable 13a is detachably connected to the light source apparatus 3.

A signal connector 16a at an end portion of a signal cable 15a extended from the connector 14a is detachably connected to the video processor 4.

The endoscope 2B is a television camera-mounted endoscope configured by an optical endoscope 10a, which is configured by an fiberscope or the like, and a television camera 10b detachably connected to an eyepiece section 17 of the optical endoscope 10a.

The optical endoscope 10a includes the insertion section 11, the operation section 12, the eyepiece section 17, and a light guide cable 13b extended from the operation section 12. A light guide connector 14b at an end portion of the light guide cable 13b is detachably connected to the light source apparatus 3. A signal connector 16b at an end portion of a signal cable 15b extended from the television camera 10b is detachably connected to the video processor 4.

Figure 2:
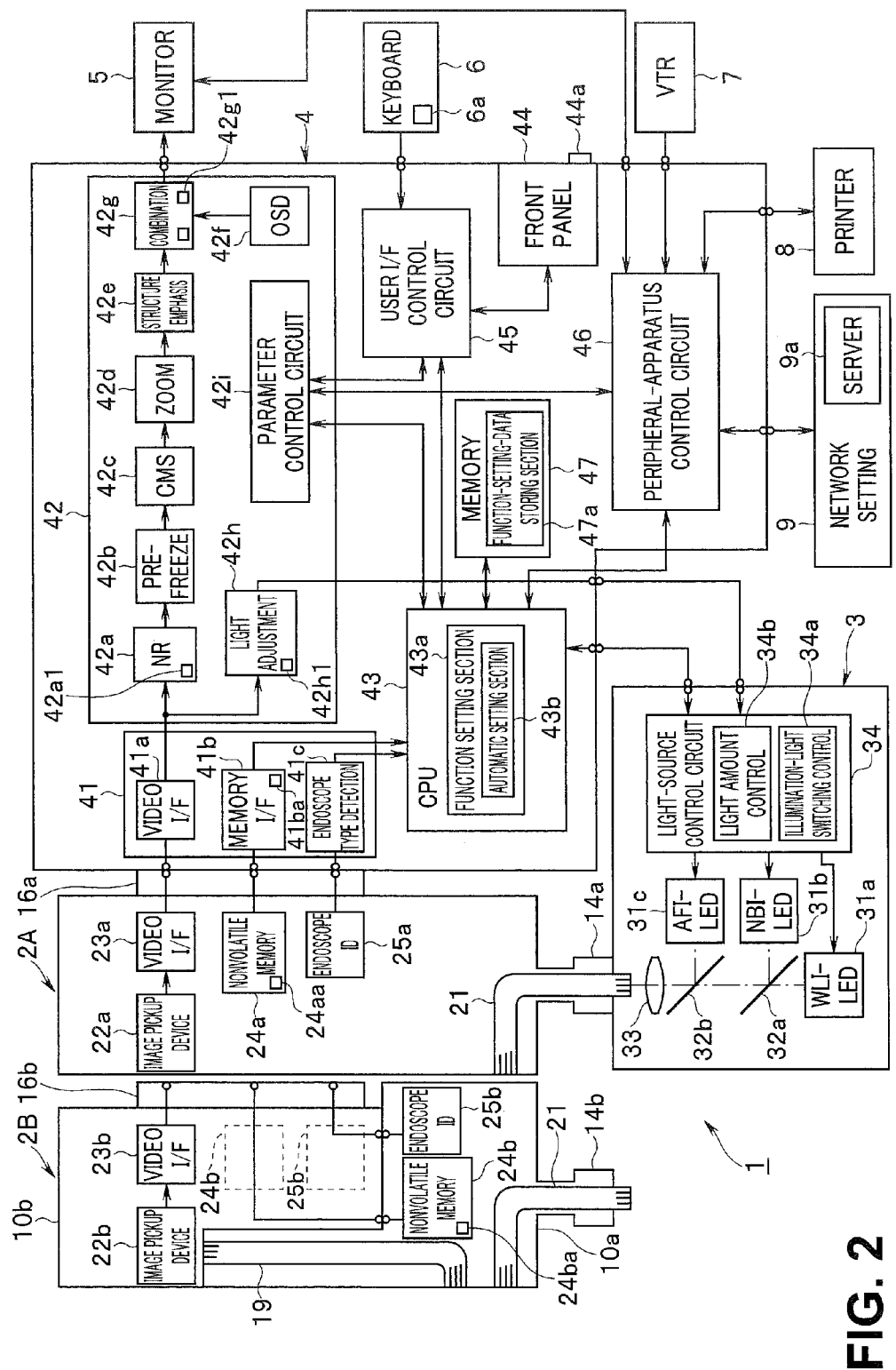
FIG. 2 is a diagram showing an internal configuration of a video processor and the like in FIG. 1.

In examples shown in FIG. 1 and FIG. 2, a state is shown in which the endoscope 2A is connected to the light source apparatus 3 and the video processor 4. However, the endoscope 2B can also be connected to the light source apparatus 3 and the video processor 4.

As shown in FIG. 2, a light guide 21 is inserted through both of the endoscopes 2A and 2B. When the connector 14a or the light guide connector 14b is connected to the light source apparatus 3, illumination light from the light source apparatus 3 is made incident on an end face of the light guide 21. The illumination light made incident on the end face is emitted from an illumination window, in which a distal end face of the light guide 21 is disposed, and illuminates an observation part or the like in the body into which the insertion section 11 is inserted.

In an observation window adjacent to the illumination window, a not-shown objective lens is disposed. In the endoscope 2A, an image pickup device 22a is disposed in an image forming position of the objective lens. On the other hand, in the endoscope 2B, a distal end face of an image guide 19 is disposed in an image forming position of an objective lens. An optical image formed on the distal end face is transmitted to a rear end face facing the eyepiece section 17 in the rear. The optical image transmitted to the rear end face is formed on an image pickup device 22b in the television camera 10b through the eyepiece section 17. The endoscope 2A includes a video interface (abbreviated as video I/F) 23a configured by a buffer circuit and the like connected to the image pickup device 22a, a nonvolatile memory 24a, and an endoscope-ID storing section (in FIG. 2, simply described as endoscope ID) 25a in which endoscope identification information (endoscope ID) including endoscope type information is stored. Note that, the endoscope type is the same meaning as an endoscope kind.

The endoscope 2B includes, for example, the image pickup device 22b and a video I/F 23b provided on the television camera 10b side and a nonvolatile memory 24b and an endoscope-ID storing section (in FIG. 2, briefly described as endoscope ID) 25b, in which endoscope identification information (endoscope ID) including endoscope type information is stored, provided on the optical endoscope 10a side.

The nonvolatile memory 24b and the endoscope-ID storing section 24b are connected to a signal line on the television camera 10b side by a signal line. The signal connector 16b at the end portion of the signal cable 15b is connected to the video processor 4, whereby the nonvolatile memory 24b and the endoscope-ID storing section 25b are respectively connected to a memory I/F 41b and an endoscope-type detection circuit 41c, which detects an endoscope and a type, of the video processor 4 (as in the case of the endoscope 2A). Note that, in the case of the endoscope 2B in which the television camera 10b mounted according to a type of the optical endoscope 10a is uniquely determined, the endoscope-ID storing section 25b indicated by a solid line provided on the optical endoscope 10a side in FIG. 2 may be provided on the television camera 10b side as indicated by a dotted line. The nonvolatile memory 24b may be provided on the television camera 10b side as indicated by a dotted line in FIG. 2.

Note that the endoscope identification information (endoscope ID) to be the endoscope type information may be stored in memory regions of the nonvolatile memories 24a and 24b.

The endoscopes 2A, 2B, . . . are configured from, for example, as shown in FIG. 3, a GIF (an upper digestive tract endoscope), a CF (a lower digestive tract endoscope), a TJF (an endoscope for duodenum), a BF (an endoscope for bronchus or respiratory organ), an ENT (an endoscope for otorhinology), and a CYF (an endoscope for urinary organ).

As shown in FIG. 2, the light source apparatus 3 includes three light sources, that is, a light emitting diode for wideband observation (abbreviated as WLI-LED) 31a, an LED for narrowband (NBI-LED) 31b, and an LED for fluorescence observation (AFI-LED) 31c, dichroic mirrors 32a and 32b, a condensing lens 33, and a light-source control circuit 34, which controls light emission of the three LEDs, to be capable of generating illumination lights corresponding to three observation modes, that is, a wideband observation mode (a WLI mode), a narrowband light observation mode (an NBI mode) and a fluorescence observation mode (an AFI mode), which form a special light observation mode. Note that, in FIG. 2, a configuration example is shown in which the LEDs are used as the light source apparatus 3. However, it is also possible to use, for example, a Xenon lamp, selectively cause light of the Xenon lamp to pass through a filter for wideband observation, a filter for narrow band, and a filter for fluorescence observation disposed in a circumferential direction of a rotatable disk, and generate illumination lights corresponding to the three observation modes.

The WLI-LED 31a generates, for example, white light that covers a visible wavelength band. The white light is transmitted through almost the entire dichroic mirror 32a, further transmitted through almost the entire dichroic mirror 32b, condensed by the condensing lens 33, and made incident on the light guide 21 as illumination light for WLI.

The NBI-LED 31b generates, for example, one or two narrow band lights in a wavelength band of blue. The narrow band lights are selectively reflected on the dichroic mirror 32a, further selectively transmitted through the dichroic mirror 32b, condensed by the condensing lens 33, and made incident on the light guide 21 as illumination lights for NBI.

The AFI-LED 31c generates excitation light in a specific wavelength band. The excitation light is selectively reflected on the dichroic mirror 32b, condensed by the condensing lens 33, and made incident on the light guide 21 as illumination light for AFI.

When selection of an observation mode is performed from the keyboard 6 or the like, a signal of the selection is transmitted from the video processor 4 to the light-source control circuit 34. The light-source control circuit 34 causes the LED corresponding to the selected observation mode to emit light. That is, the light-source control circuit 34 includes a function of an illumination-light-switching control section 34a that causes the LED corresponding to the selected observation mode to emit light.

The light-source control circuit 34 includes a function of a light-amount control section 34b that performs control of light emission amounts of the LEDs. The light-amount control section 34b adjusts the light emission amounts of the LEDs and performs light amount control with a light adjustment signal generated by a light-adjusting circuit 42h explained below.

FIG. 4 shows a plurality of selective functions to be selectively set (according to an endoscope type) in the endoscope system 1 of the present embodiment. A leftmost side in FIG. 4 indicates respective items of the selective functions. A right side of the leftmost side simply indicates, with settings A, B, and C, setting contents such as levels selectively set in the respective items. The number of the settings A, B, and C in FIG. 4 is simplified. For example, the number of settings that can selectively set changes depending on the items of the selective functions in FIG. 4. For example, a selective function in an item of luminance control is set from two functions of ON and OFF or selectively set from twenty-four functions of A1 to A8/B1 to B8/E1 to E8 in an item of structure emphasis.

As explained above, as the observation mode, for example, any observation mode can be selected from three observation modes. As the observation mode, one of the three observation modes can be set. For example, concerning noise reduction by an NR circuit 42a explained below, one of nine in OFF and levels 1 to 8 can be set.

As shown in FIG. 2, an image pickup signal picked up by an image pickup device 22i (i=a, b, . . . ) is inputted to a video I/F 41a configured by a preamplifier and a correlated double sampling processing circuit (abbreviated as CDS circuit) in the interface circuit 41 of the video processor 4 through a video I/F 23i, converted into a video signal (an image signal), and thereafter inputted to a video processing circuit 42.

The video processing circuit 42 includes a noise reduction circuit (abbreviated as NR circuit) 42a that reduces noise in a video signal, a pre-freeze circuit 42b that performs pre-freeze processing before a freeze instruction when a still image frozen by the freeze instruction is displayed, a color-management-system processing circuit (a CMS circuit or a color correction circuit) 42c corresponding to a color mode or a color processing mode, a zoom circuit 42d that performs zoom processing, a structure emphasis circuit 42e that performs structure emphasis, an on-screen display circuit (an OSD circuit) 42f that performs processing for displaying a menu screen and the like, a combination circuit 42g that combines the menu screen and the like generated by the OSD circuit 42f with a structure-emphasized video (image), a light-adjusting circuit 42h that generates a light adjustment signal, and a parameter control circuit 42i that controls parameters of the NR circuit 42a, the pre-freeze circuit 42b, . . . , and the light-adjusting circuit 42h. Note that the combination circuit 42g includes a mask circuit 42g1 that sets a size of an endoscopic image picked up by the image pickup device 22i and outputted to the monitor 5 through the video processing circuit 42.

For example, the NR circuit 42a applies, using a video signal of an immediately preceding frame (or field) and a video signal of a present frame (or field), time average processing according to a value of a parameter to be set and performs noise reduction (NR) processing for reducing random noise in an image.

As shown in FIG. 4, concerning noise reduction by the NR circuit 42a, operation of the NR circuit 42a can be set to OFF and a parameter of processing of the NR circuit 42a can be set to any level from the level 1 to the level 8. Note that, in the present embodiment, a larger value of j in a level j (j=1 to 8) indicates that processing functions of the respective circuits are larger. For example, the parameter control circuit 42i sets a function of the noise reduction of the NR circuit 42a to OFF according to a parameter for NR circuit PO and sets the levels 1 to 8 of the noise reduction according to parameters for NR circuit P1 to P8. The parameter control circuit 42i sets the other circuits described below in the same manner.

Concerning the pre-freeze circuit 42b, as shown in FIG. 4, a pre-freeze function can be set to OFF and the pre-freeze function can be set to any level from the level 1 to the level 8.

As the color mode by the CMS circuit 42c, three modes 1, 2, and 3 for performing color correction corresponding to an observation part or a type of an endoscope are prepared. For example, when an upper digestive tract is observed, since an endoscopic image easily has a slightly greenish tone, the mode 1 for correcting a greenish color to a reddish color is prepared. When a lower digestive tract is observed, since an endoscopic image has a slightly reddish tone, the mode 3 for correcting a reddish color to a greenish color is prepared. The mode 3 is prepared to observe a duodenum and the like.

As magnification for enlarging an image through electronic zoom processing by the zoom circuit 42d, 1.0 (zoom processing is OFF), 1.2, and 1.4 can be selectively set.

Concerning structure emphasis processing by the structure emphasis circuit 42e, in A/B/E serving as setting corresponding to observation modes, types of the endoscopes 2I, and the like, a level can be selectively set from the levels 1 to 8 (i.e., A1 to A8/B1 to B8/E1 to E8) respectively having different processing levels (intensities) of structure emphasis.

The mask circuit 42g1 of the combination circuit 42g can selectively set one of small, medium (Normal), and large as a mask size of an endoscopic image outputted to the monitor 5.

The light-adjusting circuit 42h generates a light adjustment signal in order to set brightness of an endoscopic image to an appropriate level. When generating the light adjustment signal, the light-adjusting circuit 42h generates light adjustment signals of the level 1 to the level 8 and outputs the light adjustment signals to the light-source control circuit 34 of the light source apparatus 3.

The light-adjusting circuit 42h includes a photometry circuit 42h1 that detects brightness of an endoscopic image. As shown in FIG. 4, the photometry circuit 42h1 can detect the brightness according to three photometry methods, that is, Peak (peak photometry), Ave (average photometry), and Auto (automatic photometry) and can select one photometry method from the three photometry methods. The peak photometry is a photometry method for detecting brightness at a peak value of a video signal. The average photometry is a photometry method for detecting brightness at an average of the video signal. The automatic photometry is an intermediate photometry method obtained by combining the peak photometry and the average photometry.

In the present embodiment, the NR circuit 42a includes a luminance control circuit 42a1 that performs luminance control such that, for example, an endoscopic image can be displayed in a wide dynamic range in the GIF mode. The luminance control circuit 42a1 may be provided in, for example, the NR circuit 42a as shown in FIG. 2 or may be provided on an outside of the NR circuit 42a and in the video processing circuit 42.

As shown in FIG. 4, the luminance control processing by the luminance control circuit 42a1 can select to set the luminance control to OFF and set the luminance control to ON.

Video related functions (or video related items) that can be selectively set are explained with reference to FIG. 4. Illumination related functions (illumination related items) are further prepared.

The light-source control circuit 34 receives the light adjustment signal of the light-adjusting circuit 42h and variably controls, with driving power for driving the LEDs, a light amount of lights emitted by the LEDs in the observation mode in operation to −8 to +8. Note that a light amount of 0 is a standard light amount.

The light adjustment and the photometry explained in the video related functions relate to illumination as well. Therefore, the light adjustment and the photometry may be changed to be included in the illumination related functions. The observation mode closely relates to the illumination related functions by the light source apparatus 3 as well.

As peripheral apparatus related functions (peripheral apparatus related items), there are a server corporation function and a peripheral apparatus control function. When the server cooperation function is turned on, the endoscope system 1 operates in a state in which the endoscope system 1 can, for example, refer to data in a server 9a configuring the network apparatus 9 and write data. When the server cooperation function is turned off, the endoscope system 1 operates irrespective of the server 9a.

Similarly, when the peripheral apparatus control is turned on, the endoscope system 1 controls, while monitoring states of peripheral apparatuses connected to the video processor 4, operation of the peripheral apparatuses. When the peripheral apparatus control is turned off, the endoscope system 1 operates irrespective of the states of the peripheral apparatuses. Note that ON and OFF of the peripheral apparatus control in FIG. 4 are ON and OFF of the VTR 7 and the printer 8 functioning as a part of the peripheral apparatuses connected via a peripheral-apparatus control circuit 46. The network apparatus 9 is connected to the video processor 4 via the peripheral-apparatus control circuit 46. However, the network apparatus 9 is controlled by a selective function of server cooperation. The monitor 5 always operates together with the video processor 4. The light source apparatus 3 always operates in cooperation with the video processor 4.

As shown in FIG. 2, the video processor 4 includes a central processing unit (abbreviated as CPU) 43 connected to the memory I/F 41b (in the interface circuit 41) that reads out memory contents of a nonvolatile memory 24i and the endoscope-type detection circuit 41c (in the interface circuit 41) that detects an endoscope type by reading out an endoscope ID, a front panel 44 that forms an input section in a user interface in conjunction with the keyboard 6, a user-I/F control circuit 45 that controls a user interface between the keyboard 6 and the front panel 44, a peripheral-apparatus control circuit 46 that controls the monitor 5, the VTR 7, the printer 8, and the network apparatus 9 that configure the peripheral apparatuses, and a memory 47 that stores various setting contents.

In the endoscope ID, for example, information on a low-order bit side for specifying respective endoscopes is further added to information on a high-order bit side representing an endoscope type. The endoscope-type detection circuit 41c detects the endoscope type from information concerning a predetermined number of bits on the high-order bit side representing the endoscope type. Note that, when data is inputted from the keyboard 6 or the like forming the input section, the CPU 43 acquires the inputted data via the user-I/F control circuit 45 and, when display is necessary, generates characters or the like for display via the OSD circuit 42f and causes the monitor 5 to display the characters or the like.

The CPU 43 controls operations of the respective sections of the video processor 4 and performs control of the entire endoscope system 1. Therefore, the CPU 43 is connected to the parameter control circuit 42i to be capable of performing transmission and reception of data such as parameters. The CPU 43 controls operations of the respective circuits of the video processing circuit 42 via the parameter control circuit 42i.

The CPU 43 is connected to the user-I/F control circuit 45 to be capable of performing transmission and reception of data. When data such as an instruction is inputted from the keyboard 6 or the front panel 44 forming the input section by a user, the CPU 43 performs, via the user-I/F control circuit 45, control operation corresponding to content of data inputted by the user.

The CPU 43 is connected to the peripheral-apparatus control circuit 46 to be capable of performing transmission and reception of data. The CPU 43 grasps states of the peripheral apparatuses connected to the peripheral-apparatus control circuit 46 and controls operations of the peripheral apparatuses via the peripheral-apparatus control circuit 46. When the peripheral apparatus is the network apparatus 9, the CPU 43 can access the server 9a of the network apparatus 9, refer to accumulated data accumulated in the server 9a, and perform writing, addition, and the like of data to the accumulated data in the server 9a on the basis of an instruction from the user. The parameter control circuit 42i is connected to the user-I/F control circuit 45 and the peripheral-apparatus control circuit 46. Operation of the parameter control circuit 42i is controlled under control by the CPU 43.

Note that the light source apparatus 3 functioning as the peripheral apparatus more often operates in close cooperation with the video processor 4 than the other peripheral apparatus. Therefore, the CPU 43 in the video processor 4 is electrically connected to the light-source control circuit 34 in the light source apparatus 3 not via the peripheral-apparatus control circuit 46.

The CPU 43 includes a function of a function setting section (or a function setting circuit or a function setting device) 43a that sets a plurality of selective functions (simply referred to as functions as well) that can be selectively set in the endoscope system 1.

The function setting section 43a of the CPU 43 includes a function of an automatic setting section 43b that automatically sets, with respect to the endoscope 2I connected to the video processor 4, according to information concerning a type of the endoscope 2I detected by the endoscope-type detection circuit 41c from an endoscope ID set in the endoscope 2I, the respective items in the plurality of selective functions shown in FIG. 4 respectively to setting states optimum or appropriate for the type of the connected endoscope 2I.

Therefore, a nonvolatile memory 47, in which data can be written and from which data can be readout by the CPU 43, has stored therein function setting data serving as association data for associating, according to the type of the endoscope 2I, a plurality of setting items, which can be selectively set, in the respective selective functions of the plurality of selective functions shown in FIG. 4 such that one each of the setting items is appropriately set. That is, the memory 47 includes a function-setting-data storing section 47a that stores function setting data (simply referred to as setting data as well) corresponding to the type of the endoscope 2I. Note that a function of setting the respective selective functions is referred to as a (endoscope) type mode as well according to the type of the endoscope 2I.

In the present embodiment, besides the (endoscope) type mode, a setting mode for setting an endoscopic examination to be able to be easily performed (by automatically setting the plurality of selective functions in the endoscope system 1 respectively to appropriate setting states) is prepared.

This is supplementarily explained below.

In the present embodiment, the respective functions in the plurality of (selective) functions in the endoscope system 1 can be respectively appropriately set according to the type of the endoscope 2I (used by being) actually connected to the video processor 4 as explained above. However, a (selective) function for smoothly performing an endoscopic examination not always depending on the type of the endoscope 2I is present. Therefore, in the present embodiment, a plurality of setting modes such as blood vessel detection besides the type mode are prepared together with the (endoscope) type mode for respectively appropriately setting the respective functions in the plurality of (selective) functions in the endoscope system 1 according to the type of the endoscope 2I.

FIG. 5 shows setting modes that can be selectively set in the endoscope system 1 of the present embodiment and overviews of the setting modes. As the setting modes, besides the (endoscope) type mode explained above, modes of blood vessel detection, GI (an endoscope for surgery)/SP (an endoscope for digestive organs) coordination, wide area, release, screening, and esophagus can be selected. The selection of the blood vessel detection and the like can be performed from the keyboard 6 or the front panel 44 forming the input section.

The blood vessel detection is a mode for detecting a blood vessel and is used in increasing contrast of the blood vessel to more clearly display the blood vessel. The GI (an endoscope for surgery)/SP (an endoscope for digestive organs) coordination is used when a GI (an endoscope for surgery) and an SP (an endoscope for digestive organs) are simultaneously used. The wide area is used when it is desired to display, in a large size, an endoscopic image displayed on a screen of the monitor 5. The wide area is effective when it is desired to view the endoscopic image in a wide screen area. The release is used when a still image is saved. The release is used when it is desired to save an image with less blur.

The screening is used when it is desired to carry out an endoscopic examination in a short time. (The setting mode of) the esophagus is used when it is desired to mainly perform observation of an esophagus.

(The function-setting-data storing section 47a of) the memory 47 has also stored therein, besides the function setting data associated with the type of the endoscope explained above, second function setting data respectively corresponding to the modes of the blood vessel detection, the GI (an endoscope for surgery)/SP (an endoscope for digestive organs) coordination, the wide area, the release, the screening, and the esophagus. Note that the second function setting data may be stored in a memory region in the memory 47 on an outside of the function-setting-data storing section 47a or a storage device such as a memory separate from the memory 47.

For example, the automatic setting section 43b of the CPU 43 automatically sets, besides automatically setting, on the basis of a detection result of the type of the endoscope, the plurality of selective functions of the endoscope system 1 to appropriate setting states for the detected type of the endoscope, the plurality of selective functions of the endoscope system 1 to appropriate setting states according to selection of the modes of the blood vessel detection, the GI (an endoscope for surgery)/SP (an endoscope for digestive organs) coordination, the wide area, the release, the screening, and the esophagus.

In the present embodiment, in order to make it possible to appropriately set the selective functions of the endoscope system 1 with respect to the setting modes in FIG. 5 as explained above, the function setting data and the second function setting data serving as association data for respectively appropriately setting the plurality of selective functions in the endoscope system 1 according to information such as the (endoscope) type are stored in the memory 47 explained above or the like in advance.

FIG. 6 shows a part of the function setting data stored in the function-setting-data storing section 47*a* in advance. The function-setting-data storing section 47*a* has stored therein table data for respectively appropriately setting, for example, the setting values of the items of the respective selective functions such as the observation mode and the noise reduction shown in FIG. 4 according to GIF, TJF, . . . (in FIG. 5, described as a Gif mode, a TJF mode, . . . ) representing types of the endoscopes 2I as shown in FIG. 6.

For example, the function-setting-data storing section 47*a* has stored therein function setting data for setting the observation mode to the WLI, setting the noise reduction to the level 2, setting the pre-freeze to the level 6, setting the color mode to a mode "a", . . . , setting the light amount to 0 (a standard light amount level), setting the server cooperation to ON, and setting the peripheral apparatus control to ON according to the endoscope type of the GIF.

The function-setting-data storing section 47*a* has stored therein function setting data for setting, when the endoscope 2I is the TJF, the observation mode to the WLI, setting the noise reduction to the level 2, setting the pre-freeze to the level 6, setting the color mode to the mode 3, . . . , setting the light amount to +2, setting the server cooperation to ON, and setting the peripheral apparatus control to ON according to the endoscope type of the TJF.

Therefore, when the type of the endoscope 2I connected to the endoscope-type detection circuit 41*c* of the video processor 4 is, for example, the GIF, the automatic setting section 43*b* of the CPU 43 acquires, referring to the function setting data stored in the function-setting-data storing section 47*a*, function setting data corresponding to the endoscope type of the GIF (more specifically, function setting data in which the observation mode is the WLI, the noise reduction is the level 2, the pre-freeze is the level 6, the color mode is the mode 1, . . . , the light amount is 0, the server cooperation is ON, and the peripheral apparatus control is ON) and automatically sets states of the plurality of selective functions of the endoscope system 1 to states of the acquired function setting data.

As more specifically shown in FIG. 6, the automatic setting section 43*b* of the CPU 43 automatically sets, according to a detection result of the endoscope type, the plurality of functions such as the noise reduction in the video processor 4 functioning as the signal processing apparatus configuring the endoscope system 1, for example, a light amount in the light source apparatus 3 forming the peripheral apparatus, and the like respectively to appropriate setting states.

In this way, the plurality of selective functions of the endoscope system 1 can be automatically set to the appropriate setting states according to the detected type of the endoscope 2I and the like. Consequently, it is possible to make it unnecessary for a surgeon to consume labor and time for respectively manually selecting the plurality of selective functions and setting the selected selective functions respectively to appropriate setting states and improve operability.

In the present embodiment, the automatic setting section 43*b* includes a function of appropriately automatically setting, according to the type of the endoscope 2I, selective functions according to other setting modes as shown in FIG. 5 and FIG. 6 besides the function (endoscope) type mode for setting the selective functions of the endoscope system 1. FIG. 6 shows a specific example of function setting data in the case in which, for example, the mode of the blood vessel detection is selected. For example, in the memory 47, function setting data for blood vessel detection for setting a plurality of functions to make it easy to appropriately perform the blood vessel detection respectively is stored. When the mode of the blood vessel detection is selected from the input section, the plurality of functions are automatically set as in the function setting data for blood vessel detection. In this case, the type of the endoscope 2I is not set (i.e., the mode of the blood vessel detection does not depend on the type of the endoscope 2I). Note that, similarly, the release and the screening do not depend on the type of the endoscope 2I.

In the present embodiment, a specific function key 6*a* and a specific function button 44*a* are respectively set in advance in the keyboard 6 and the front panel 44. By operating the specific function key 6*a* or the specific function button 44*a*, it is possible to collectively display, on the monitor 5, (a list of) setting contents of the plurality of selective functions currently set in the endoscope system 1. Note that the monitor 5 forms a display section that displays, for example, a list of setting contents of a plurality of functions set by the function setting section 43*a*.

For example, during use of the endoscope system 1 in a state in which the type of the endoscope is the GIF, when the specific function key 6*a* or the specific function button 44*a* is operated, the CPU 43 identifies the operation of the specific function key 6*a* or the specific function button 44*a* via the user-I/F control circuit 45 and performs control to display the selective functions in the setting state corresponding to the GIF mode shown in FIG. 5 on the monitor 5.

It is possible to change the function setting contents in FIG. 5 according to a preference or the like of the user from the keyboard 6 and the front panel 44. In general, the function setting data shown in FIG. 5 is optimally close to the type of the endoscope. However, it could occur that the function setting data does not correspond to preferences of individual users. Therefore, the function setting contents can be changed. In other words, the keyboard 6 and the front panel 44 forming the input section includes a function of a function-setting changing section that can change the contents of the function setting set by the automatic setting section 43*b* or the function setting section 43*a*.

Even when the user changes the function setting contents, the user can change the function setting contents in a state in which the setting contents of the selective functions are collectively displayed on the monitor 5 by the operation of the specific function key 6*a* or the specific function button 44*a*. Therefore, it is possible to easily set the function setting contents to setting states desired by the user.

In the present embodiment, by operating a function menu button or a function menu key set in the keyboard 6 and the front panel 44, the user can display a function menu as shown in FIG. 7 on the monitor 5 and perform setting of changes of various functions including the selective functions from the displayed function menu and perform setting such as addition of separate selective functions anew.

In an example shown in FIG. 7, a video related function, an illumination related function, a peripheral apparatus related function, and an observation mode function are the functions explained with reference to FIG. 4 and FIG. 5. In FIG. 7, an observation part (or a medical department) related function is added.

As explained above, it is possible to automatically set, according to the type of the endoscope, the plurality of kinds of selective functions to function setting contents suitable for the type. However, according to information concerning an observation part (or a medical department), it is also possible to set the plurality of kinds of selective functions to function setting contents suitable for the observation part (or the medical department) and change the set function setting contents.

Note that, in the observation part (or the medical department) related function, otorhinology, urology, an upper digestive tract, a lower digestive tract, and a bronchus other than bile/pancreatic ducts respectively generally correspond to the cases of the ENT, the CYF, the GIF, the CF, and the BF corresponding to the otorhinology, the urology, the upper digestive tract, the lower digestive tract, and the bronchus in an endoscope type. In other words, the user such as the surgeon can perform setting of a check and a change of setting contents in the type mode of the endoscope and check and change similar setting contents from the observation part related function.

In the present embodiment, the memory I/F 41b in the video processor 4 includes a data read/write circuit 41ba including a function of reading out data of the nonvolatile memory 24i of the endoscope 2I and a function of writing data. As explained below, it is possible to store, in the nonvolatile memory 24i of the endoscope 2I, setting data for setting the plurality of functions in the endoscope system 1 respectively to appropriate setting states in the case of the endoscope 2I.

The endoscope system 1 of the present embodiment includes a plurality of types of the endoscopes 2I, the video processor 4 forming the signal processing apparatus to which one endoscope among the plurality of types of the endoscopes 2I is connected, the signal processing apparatus performing video processing for an output signal of the image pickup device 22i mounted on the connected endoscope, the light source apparatus 3, the monitor 5, the VTR 7, the printer 8, and the network apparatus 9 forming one or more peripheral apparatuses connected to the signal processing apparatus, the endoscope-type detection circuit 41c forming the endoscope-type detecting section that detects a type of the endoscope 2I when the endoscope 2I is connected to the signal processing apparatus, and the function setting section 43a that sets a plurality of functions in the endoscope system 1 including the signal processing apparatus, the endoscope 2I connected to the signal processing apparatus, and the peripheral apparatuses. The function setting section 43a automatically sets the plurality of functions respectively to appropriate setting states according to the type of the endoscope 2I detected by the endoscope-type detecting section.

Operation of the present embodiment is explained with reference to FIG. 8.

As shown in FIG. 1, the user such as the surgeon connects the endoscope 2I such as the endoscope 2A of a type corresponding to an observation part to the video processor 4 and connects the light source apparatus 3, the monitor 5, the VTR 7, and the like functioning as the peripheral apparatuses to the video processor 4 to set the endoscope system 1 to an operation state.

In first step S1, when the endoscope 2I is connected to the video processor 4, the endoscope-type detection circuit 41c detects a type of the connected endoscope 2I and sends data of the detected type to the function setting section 43a of the CPU 43.

In step S2, (the function setting section 43a of) the CPU 43 reads out, using the data of the detected type, the setting data of the plurality of selective functions in the endoscope system 1 corresponding to the data of the type from the memory 47. For example, when the data of the type is the GIF, the function setting section 43a reads out the setting data of the setting values and the like of the selective functions in a row of the GIF (mode) shown in FIG. 6 (the observation mode is the WLI, the noise reduction level is the level 2, . . . , and the peripheral apparatus control is ON). As shown in step S3a, (the function setting section 43a of) the CPU 43 determines whether a list of the read-out setting data such as the setting values of the selective functions is displayed on the monitor 5.

In step S3a after processing in step S2, when input operation for displaying the list of the allocated setting data is performed in the specific function key 6a or the specific function button 44a, (the function setting section 43a of) the CPU 43 performs control to display the list of the setting data on the monitor 5 as shown in step S3b and thereafter shifts to step S4. On the other hand, when the surgeon does not perform input operation from the specific function key 6a or the like, (the function setting section 43a of) the CPU 43 shifts to processing in step S4 without performing processing shown in step S3b. In the present embodiment, it is possible to select to display or not to display the list of the setting data.

In step S4, (the function setting section 43a of) the CPU 43 performs display for requesting the surgeon to determine whether the setting data does not have to be changed.

When the selective functions of the endoscope system 1 are operated in contents of the list of the setting data displayed on the monitor 5, the surgeon performs, from the keyboard 6 or the like, an input to the effect that the setting data does not have to be changed. Then, as shown in step S5, (the function setting section 43a of) the CPU 43 respectively controls the selective functions of the video processing circuit 42, the light source apparatus 3, and the peripheral apparatuses via the parameter control circuit 42i, the light-source control circuit 34, and the peripheral-apparatus control circuit 46 to operate the selective functions of the endoscope system 1 in the contents of the list of the setting data displayed on the monitor 5. That is, (the function setting section 43a of) the CPU 43 automatically sets the plurality of selective functions of the endoscope system 1 to appropriate operation states of the setting data corresponding to the data of the detected type.

(The function setting section 43a of) the CPU 43 automatically sets the plurality of selective functions in the endoscope system 1 respectively to appropriate setting values or the like according to the type of the endoscope 2I connected to the video processor 4 and sets the endoscope system 1 in a state in which an endoscopic examination is easily performed.

As shown in step S6, (the function setting section 43a of) the CPU 43 determines whether input operation of designation of a setting mode such as the blood vessel detection other than the (endoscope) type mode is performed from the keyboard 6 or the front panel 44.

When the designation of the setting mode is performed, as shown in step S7, (the function setting section 43a of) the CPU 43 sets the endoscope system 1 to a setting state corresponding to the setting mode. For example, when the type of the endoscope 2I is the GIF, in step S5, the endoscope system 1 is automatically set to a setting state of the setting data corresponding to the GIF mode in FIG. 6. However, when designation of the setting mode of the blood vessel detection is performed in step S6, (the function setting section 43a of) the CPU 43 automatically sets (changes) the endoscope system 1 to a setting state of the setting data corresponding to the blood vessel detection mode in FIG. 6.

In this way, it is possible to establish a state in which the endoscopic examination can be performed easily and smoothly. After step S7, as shown in step S8, the surgeon performs the endoscopic examination. When the designation of the setting mode other than the type mode is not performed in step S6, (the function setting section 43a of) the CPU 43 performs processing in step S8 without performing processing in step S7.

On the other hand, when the surgeon desires to change setting data, which is (normally) appropriate setting, to appropriate setting data corresponding to a preference or the like of the surgeon obtained by changing a part of the setting data, the surgeon performs, from the keyboard 6 or the like, an input of NO (or change) in response to the determination in step S4 concerning whether the setting data does not have to be changed.

Then, as shown in step S9, (the function setting section 43a of) the CPU 43 performs control to perform display for urging designation of an item of a selective function desired to be changed. The surgeon operates a moving key or the like of the keyboard 6 and designates the item of the selective function desired to be changed.

Then, as shown in step S10, (the function setting section 43a of) the CPU 43 displays a list of setting contents that can be changed such as setting values that can be selected in the item. The surgeon designates a setting value or the like desired by the surgeon from the list, operates a decision key or the like in the keyboard 6 or the like, and decides the setting value or the like.

As shown in the next step S11, (the function setting section 43a of) the CPU 43 receives a change of one item according to the operation of the decision key or the like and performs control to perform display concerning whether a change is further performed. When the surgeon desires to further perform a change, the surgeon performs, from the keyboard 6 or the like, operation to the effect that a change is performed. In this case, returning to processing in step S9, the surgeon can change a setting value or the like of an item of a selective function that the surgeon further desires to change.

In this way, for all the selective functions of the endoscope system 1, the surgeon can change one or a plurality of items of selective functions that the surgeon desires to change. When the surgeon has changed all the items desired to be changed, the surgeon performs, from the keyboard 6 or the like, operation to the effect that a change is not performed in response to the determination concerning whether a change is performed (or not) in step S11.

Then, as shown in step S12, as in the case of step S5, (the function setting section 43a of) the CPU 43 performs setting of the respective selective functions of the endoscope system 1 as shown in the list of the changed setting data of the selective functions.

As shown in step S13, (the function setting section 43a of) the CPU 43 performs control to perform display for determining whether the changed setting data of the selective functions is saved as setting data for the user to be used by the surgeon.

When the surgeon desires to use the changed setting data for an endoscopic examination in future, the surgeon performs, from the keyboard 6 or the like, operation to the effect that the setting data is saved. Then, as shown in step S14, (the function setting section 43a of) the CPU 43 saves (stores), in the memory 47, the changed setting data as setting data to which a user name of the surgeon is added.

In this case, in the memory 47, setting data (association data) corresponding to the user name as shown in FIG. 9 is added and stored as the setting data (association data) as shown in FIG. 6.

FIG. 9 shows a part of setting data (association data) corresponding to the case in which the user name of the surgeon is a user A. In FIG. 9, setting data (association data), in which the surgeon changes only a level of the noise reduction (changes the level 2 to the level 3) as a selective function using, for example, the endoscope 2I of the type of the GIF, is added and saved (stored). In FIG. 9, setting data (association data) without designation of user names (indicated by -) is setting data used in common to all users and is the same as the setting data in FIG. 6.

In step S15 after processing in step S14, (the function setting section 43a of) the CPU 43 uses, besides the type of the endoscope 2I, the user name for the setting of the selective functions of the endoscope system 1. After processing in step S15, (the function setting section 43a of) the CPU 43 shifts to processing in step S6. When selecting not to save the changed setting data in step S13, (the function setting section 43a of) the CPU 43 also shifts to the processing in step S6.

During processing of the endoscopic examination in step S8 explained above, as shown in step S16, the CPU 43 determines whether operation for an examination end is performed from the keyboard 6 or the like. When the operation for the examination end is not performed, the CPU 43 continues the endoscopic examination in step S8. When the operation for the examination end is performed, the CPU 43 ends the processing in FIG. 8.

When the setting data corresponding to the user name is saved as explained above, (the function setting section 43a of) the CPU 43 performs setting of the selective functions of the endoscope system 1 referring to the setting data corresponding to the user name besides the type of the endoscope 2I.

Figure 8:
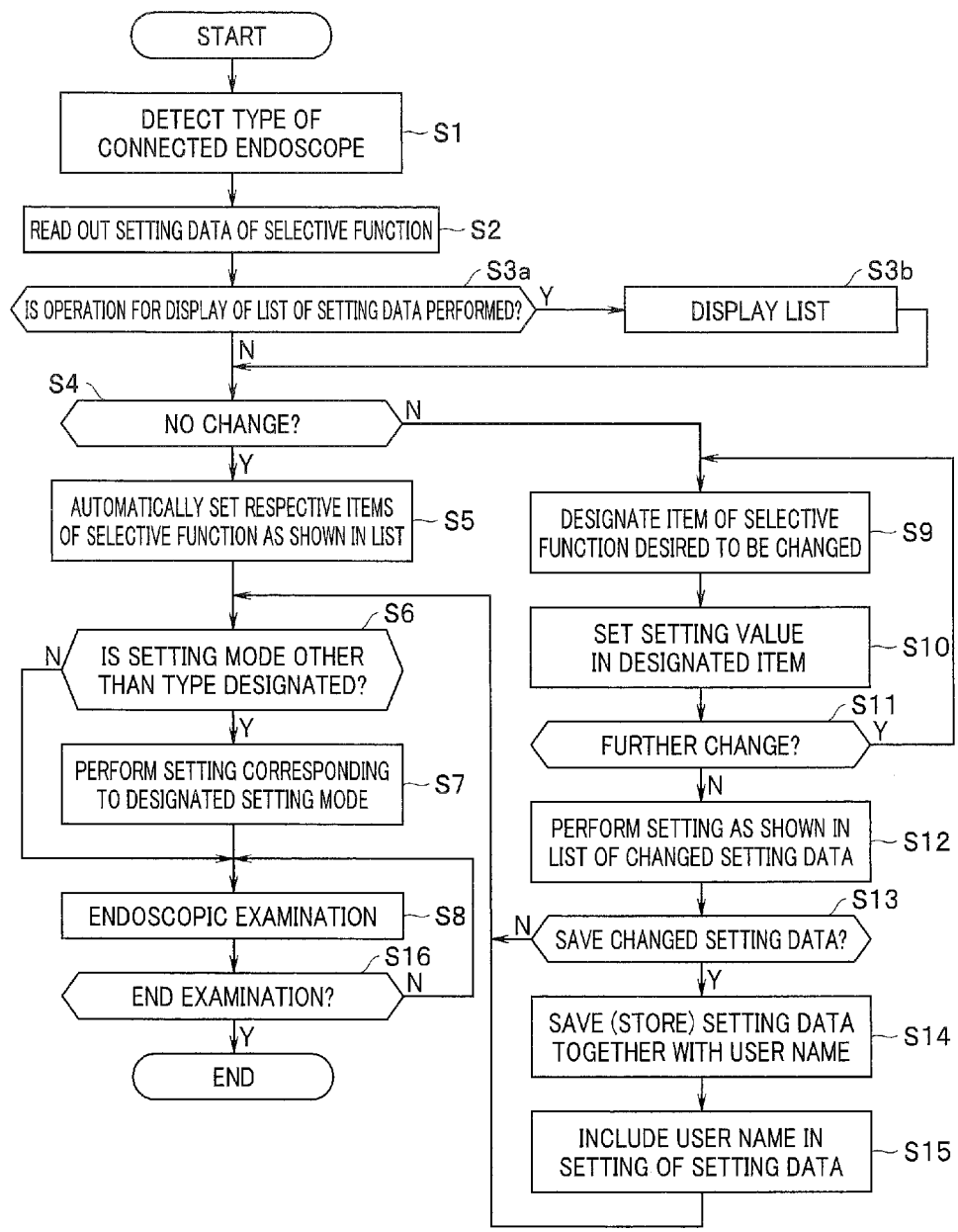
FIG. 8 is a flowchart showing processing contents in representative operation of the first embodiment.

Note that, in FIG. 8, an example is explained in which the setting data corresponding to the user name is saved in the memory 47. However, the setting data corresponding to the user name may be stored in the nonvolatile memory 24i (i=a, b, . . . ) of the endoscope 2I or may be stored in both the memories 47 and 24i. Setting data in which a user name is not set may be stored in the nonvolatile memory 24i such that all the users can use the setting data.

When the setting data corresponding to the user name or the like is stored in the nonvolatile memory 24i of the endoscope 2I, even when the endoscope system 1 is formed using a video processor (referred to as 4B) having a function different from the function of the video processor 4 in FIG. 2, setting data for a plurality of types of video processors having different functions may be stored such that the setting data can be appropriately set in the same manner. In the following explanation, a type of the video processor 4 in FIG. 2 is represented as D and a type of the video processor 4B having a function different from the function of the type D is represented as E.

FIG. 10 shows a part of setting data in the case in which the setting data is stored in, for example, a data storing section of the nonvolatile memory 24i of the endoscope of the GIF. In FIG. 2, data storing sections formed by memory regions where the setting data as shown in FIG. 10 is stored in the nonvolatile memories 24a and 24b are respectively indicated by 24aa and 24ba.

In an example shown in FIG. 10, setting data for common use, in which a user name is not set, is stored together with setting data in which user names of two users are respectively appropriately set to correspond to the users A and B. The data storing section of the nonvolatile memory 24i has stored therein, in association with the types D and E, setting data (for video processor types) corresponding to the types D and E of the video processor 4 forming the signal processing apparatus. Note that, in FIG. 10, the video processor is represented by being simplified as VP.

For example, when the type of the video processor 4 shown in FIG. 2 is D as explained above, as shown in FIG. 10, setting data corresponding to the type D of the video processor 4 is stored in the nonvolatile memory 24i of the endoscope of the type of the GIF. In the video processor 4B of the type E different from the type D of the video processor 4 shown in FIG. 2, setting data is stored in association with data of the type E of the video processor 4B such that the setting data can be automatically set to appropriate setting data and used. Note that, in the type E of the video processor 4B in FIG. 10, since the type E is a type not including, for example, the function of the pre-freeze, setting data for setting the function of the pre-freeze is absent (- indicates that the setting data is absent).

On the other hand, the memory 47 of the video processor 4 of the type D has saved (stored) therein setting data excluding setting data in the case of the type E different from the type D in FIG. 10 and further has stored therein, concerning the type of the endoscope 2I other than the GIF as well, setting data similar to the setting data in FIG. 10.

Figure 11:
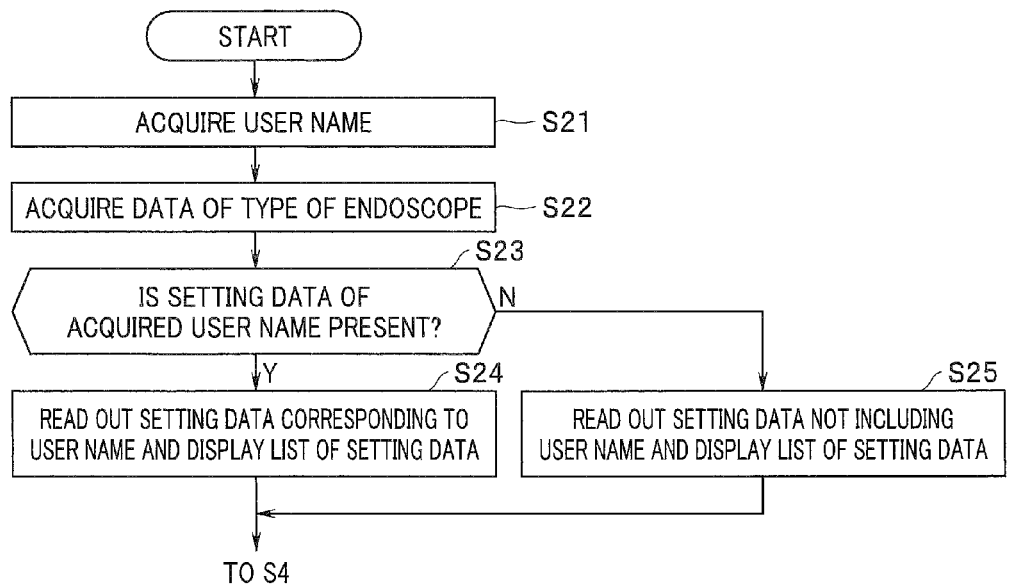
FIG. 11 is a flowchart showing a part of processing contents for appropriately setting the selective functions according to user names besides the types of the endoscope.

When the setting data set as shown in FIG. 10 is used, the endoscope system 1 performs processing slightly different from the processing shown in FIG. 8. FIG. 11 shows a part of the processing performed when the setting data as shown in FIG. 10 is used.

In the first step S21, (the function setting section 43a of) the CPU 43 performs control to perform display for urging an input of a user name of the surgeon and acquires data of the user name inputted from the keyboard 6 or the like.

In the next step S22, (the function setting section 43a of) the CPU 43 acquires data of the type of the endoscope 2I connected to the video processor 4 detected by the endoscope-type detection circuit 41c. Further, in step S23, (the function setting section 43a of) the CPU 43 determines whether setting data of the user name acquired in step S21 is present.

In the case of the data in FIG. 10, the setting data associated with the user A is stored in the memory 47. In step S24, (the function setting section 43a of) the CPU 43 performs control to read out, from the memory 47, setting data in the case in which the user name is the user A and the video processor 4 is the type D in FIG. 10 and display a list of the setting data on the monitor 5.

That is, when determining in step S23 that the user name acquired in step S21 is present, in step S24, (the function setting section 43a of) the CPU 43 performs control to read out, from the memory 47, setting data corresponding to the type D of the video processor in the user name and display a list of the read-out setting data on the monitor 5. After processing in step S24, (the function setting section 43a of) the CPU 43 shifts to step S4 in FIG. 8 and perform the processing in steps S4 and subsequent steps in FIG. 8.

If the setting data saved together with the user name acquired in step S21 is absent in step S23, as shown in step S25, common data, in which a user name is not designated, is read out (substantially the same as step S3 in FIG. 8. However, step S25 can also be applied in the case of the type E different from the type D of the video processor 4 in FIG. 2). A list of the setting data is displayed on the monitor 5. After processing in step S25, (the function setting section 43a of) the CPU 43 shifts to step S4 in FIG. 8. When the setting data associated with the user name is present, the processing in steps S23 to S25 in FIG. 11 represents that the setting data associated with the user name is more preferentially used for the setting of the plurality of functions of the endoscope system 1 than the setting data not including the user name.

Note that, in the processing in FIG. 8 explained above, when the surgeon attempts to change the setting data with respect to the display of the list of the setting data in step S4, the surgeon designates an item of a selective function to be changed from the displayed list of the selective functions to perform the change. However, the surgeon may, for example, access the server 9a of the network apparatus 9, acquire recommended setting data recommended in the function setting accumulated in the server 9a, and change the setting data with the recommended setting data and use the setting data.

Figure 12:
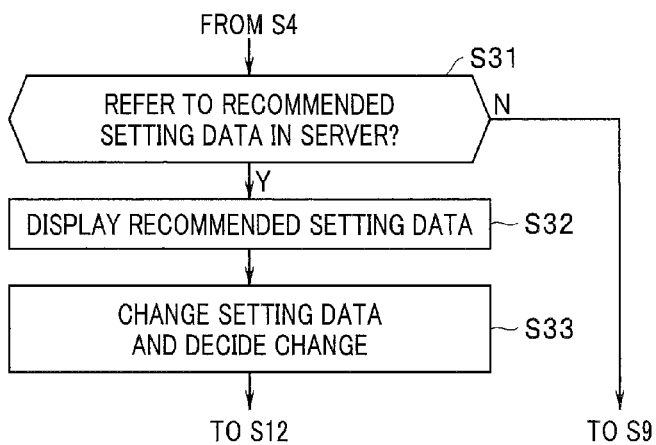
FIG. 12 is a flowchart showing processing in the case in which a plurality of functions of the endoscope system are set to appropriate setting states with reference to data accumulated in a server.

FIG. 12 shows a part of processing in this case.

When the selection to change (the input of NO in response to the determination concerning whether the setting data does not have to be changed) is performed in step S4 in FIG. 8, as shown in step S31 in FIG. 12, (the function setting section 43a of) the CPU 43 performs control to perform display concerning whether the recommended setting data to be recommended accumulated in the server 9a of the network apparatus 9 is referred to (or acquired).

When attempting to refer to the recommended setting data, the surgeon performs, from the keyboard 6 or the like, an input (selection) to the effect that the recommended setting data is referred to. In this case, as shown in step S32, (the function setting section 43a of) the CPU 43 performs control to display the recommended setting data on the monitor 5, for example, beside the list of the setting data in step S3.

As shown in step S33, the surgeon changes the setting data referring to the recommended setting data, decides change contents, and thereafter shifts to processing in step S12 in FIG. 8.

On the other hand, when not referring to the recommended setting data, the surgeon performs, from the keyboard 6 or the like, an input (selection) to the effect that the recommended setting data is not referred to. In this case, the surgeon shifts to the processing in step S9 in FIG. 8. When processing in FIG. 12 is included in the processing in FIG. 8, the selective functions of the endoscope system 1 can be set to setting data reflecting the recommended setting data accumulated in the server 9a.

Note that, in the above explanation, when the endoscope 2I is connected to the video processor 4, the type of the connected endoscope 2I can be detected. However, it could occur that an endoscope adopting a different type detection method or a different connector shape, which cannot be detected by the endoscope-type detection circuit 41c of the video processor 4, is connected.

Figure 13:
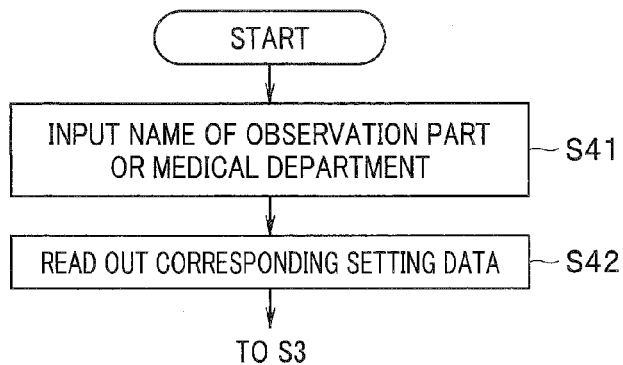
FIG. 13 is a flowchart showing a part of processing in the case in which the plurality of functions of the endoscope system are set to the appropriate setting states according to an input of a name of an observation part or a medical department.

In such a case, as shown in FIG. 13, the plurality of selective functions of the endoscope system 1 may be set to appropriate setting states.

As shown in step S41, the surgeon inputs, from the keyboard 6 or the front panel 44 configuring the input section, a name of an observation part or a medical department of an endoscope connected to the video processor 4. Setting data recommended in the observation part or the medical department of the inputted name is stored in the memory 47.

As shown in step S42, (the function setting section 43a of) the CPU 43 reads out the recommended setting data from the memory 47. After processing in step S42, (the function setting section 43a of) the CPU 43 proceeds to the processing in step S3 in FIG. 8. In this way, (the function setting section 43a of) the CPU 43 sets the selective functions of the endoscope system 1 to appropriate setting states.

Note that processing shown in FIG. 13 is processing performed alternately with the type detection of the endoscope 2I in FIG. 8. In the processing in FIG. 8, processing in steps S41 and S42 may be included. For example, when the processing in FIG. 8 is started, (the function setting section 43a of) the CPU 43 monitors whether a detection result of the type of the endoscope 2I is inputted from the endoscope-type detection circuit 41c within a predetermined time.

When the detection result of the type is inputted within the predetermined time, (the function setting section 43a of) the CPU 43 may proceed to the processing in step S2. When the detection result of the type is not inputted within the predetermined time, (the function setting section 43a of) the CPU 43 may perform control to display to the effect that the detection result is not inputted, perform the processing in steps S41 and S42 in FIG. 13, and thereafter proceed to the processing in step S3 in FIG. 8.

Figure 14:
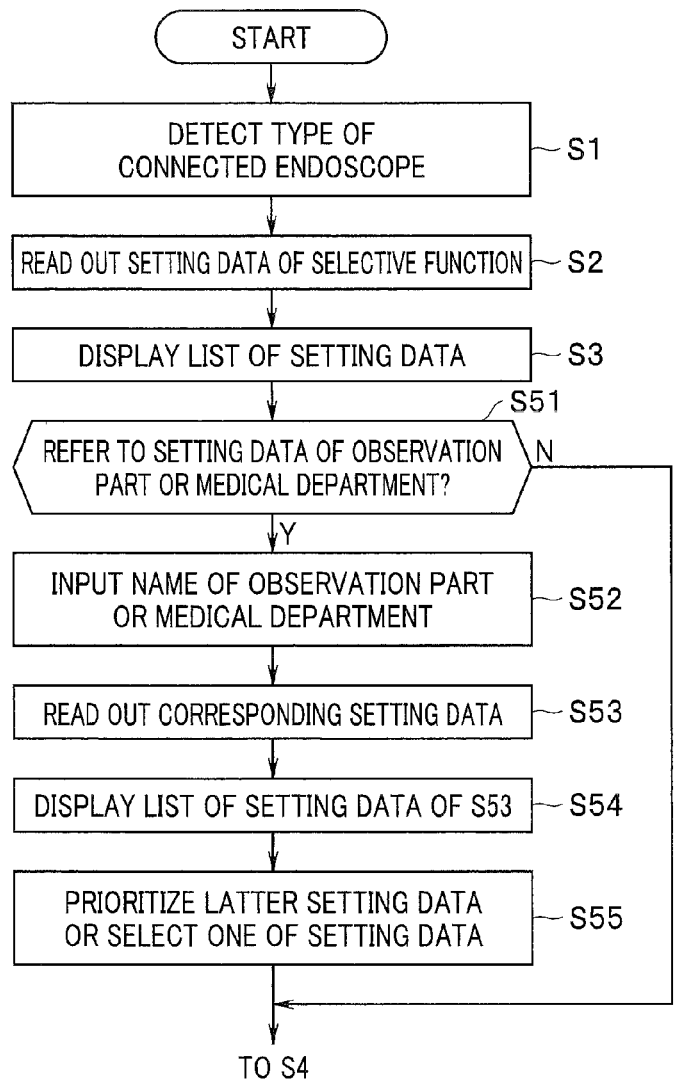
FIG. 14 is a flowchart showing a part of processing in the case in which the plurality of functions of the endoscope system are set to the appropriate setting states by making it possible to refer to setting data corresponding to an observation part and the like together with setting data corresponding to a detection result of the type of the endoscope.

(The function setting section 43a of) the CPU 43 may perform processing shown in FIG. 14 without performing the alternative processing. FIG. 14 shows processing in which only a part in FIG. 8 is changed. After performing the processing in steps S1 to S3 in FIG. 8, in step S51, (the function setting section 43a of) the CPU 43 performs control to perform display for the surgeon to select whether setting data by an observation part or a medical department is referred to.

When attempting to refer to the setting data by the observation part or the medical department, the surgeon selects to refer to the setting data. When not desiring to refer to the setting data, the surgeon selects not to refer to the setting data. When selecting not to refer to the setting data, the surgeon shifts to the processing in step S4. In the case of this selection, processing is the same as the processing in FIG. 8.

On the other hand, when selecting to refer to the setting data, in step S52, (the function setting section 43a of) the CPU 43 performs control to perform display for urging the surgeon to input a name of the observation part or the medical department. The surgeon inputs the name of the observation part or the medical department.

When the name of the observation part or the medical department is inputted, in step S53, (the function setting section 43a of) the CPU 43 reads out setting data corresponding to the name. Further, in step S54, (the function setting section 43a of) the CPU 43 displays a list of the setting data read out in step S53, for example, to be adjacent to, for example, the list in step S3.

In step S55, (the function setting section 43a of) the CPU 43 prioritizes, in the list of the setting data in step S3 and the list of the setting data in step S53, the setting data of the latter (S53) (because of a reason described below) or selects (the list of) one setting data conforming to a selection instruction by the surgeon and thereafter shifts to the processing in step S4.

The setting data based on the detection result of the type of the endoscope 2I and the setting data based on the name of the observation part or the medical department are often almost the same. However, the setting data based on the name of the observation part sometimes could be more limited contents.

For example, when a type of an upper digestive tract endoscope is detected, an esophagus and a stomach are observation targets (examination targets). However, when a name of the esophagus is designated as an observation part, it is more desirable setting to adopt setting data suitable for only an examination of the esophagus.

In such a case, the setting data based on the name of the observation part may be more preferentially adopted as setting data (to be used for setting of selective functions of the endoscope system 1) than the setting data based on the detection result of the type of the endoscope 2I. In the case of the name of the medical department, the setting data is almost the same as the setting data based on the detection result of the type of the endoscope 2I. Therefore, FIG. 14 shows processing for treating the name of the medical department in the same manner as the name of the observation part. However, only the case of the name of the observation part may be prioritized.

Note that the processing contents in FIG. 8 are explained as the operation in the case in which the endoscopic inspection is performed using the endoscope system 1. However, processing excluding steps S8 and S16 in FIG. 8 may be performed. In other words, steps S1 to S7 and S9 to S15 in FIG. 8 may be performed as pre-processing for performing the endoscopic examination, update processing for the setting data, processing for registration of new setting data, or the like.

According to the present embodiment in which the operation is performed as explained above, it is possible to automatically set the plurality of functions of the endoscope system 1 to appropriate setting states according to a type of an endoscope actually in use.

According to the present embodiment, it is possible to automatically set the plurality of functions of the endoscope system 1 to appropriate setting states according to the endoscope type mode that depends on the type of the endoscope. It is possible to automatically set the plurality of functions of the endoscope system 1 to appropriate setting states according to the setting mode such as the blood vessel detection that does not depend on the type of the endoscope.

According to the present embodiment, it is possible to store setting data for setting the plurality of functions of the endoscope system 1 to appropriate setting states reflecting preferences of individual users together with setting data for setting the plurality of functions of the endoscope system 1 to appropriate setting states for common users without reflecting the preference of the users. After storing the setting data, it is possible to preferentially use the setting data.

According to the present embodiment, it is possible to acquire the recommended data accumulated in the server 9a and use the recommended data as setting data for setting the plurality of functions of the endoscope system 1 to appropriate setting states.

In the present embodiment, setting data explained below may be stored or the stored setting data may be registered to be capable of being used.

In FIG. 10, it is explained that the setting data for setting, in each of the plurality of types of the video processors 4 and 4B to which the endoscope 2I is connected to be used, the video processor to the appropriate setting state is stored in the nonvolatile memory 24i of the endoscope 2I and thereafter registered to be capable of being used. However, as shown in FIG. 15, setting data in the case in which light source apparatuses of different types are used may be further stored.

FIG. 15 further shows a part of setting data corresponding to light source apparatuses 3 and 3B of types G and H in FIG. 10. In FIG. 15, in the case of the same user A, even if the type D of the video processors is the same, since the types G and H of the light source apparatuses are different, setting values of light amounts set to different values 0 and +1. When the setting data shown in FIG. 15 is used, even when the types of the endoscopes 2I, the types of the video processors functioning as the signal processing apparatuses, or the types of the light source apparatuses are different, it is possible to automatically set the endoscopes 2I, the video processors, or the light source apparatuses respectively to appropriate setting states and smoothly perform the endoscopic examination.

Note that, in FIG. 15, a part of setting data in the case in which the type of the endoscope 2I is the GIF is shown. Naturally, in nonvolatile memories of the other types of endoscopes, setting data for respectively appropriately setting the plurality of functions in the endoscope system 1 according to the types of the endoscopes are stored. On the video processors 4 and 4B side, setting data corresponding to types of the light source apparatuses 3 and 3B connected to the video processors and used may be stored together with the types of the endoscopes 2I connected and used.

Note that, in the embodiments explained above, setting states of the plurality of peripheral apparatuses connected to the video processor 4 are not illustrated. However, the setting states of the plurality of peripheral apparatuses may be illustrated according to operation of the specific function key 6a, the specific function button 44a explained above, or the like.

Only the setting contents of the plurality of peripheral apparatuses may be collectively displayed according to a case in which the number of selective functions in the video processor 4 functioning as the signal processing apparatus is large. Therefore, the types and the setting items of the peripheral apparatuses acquired by the peripheral-apparatus control circuit 46 from the peripheral apparatuses through communication or the like as shown in FIG. 16 may be acquired by operation of a button for peripheral apparatuses set in advance in the keyboard 6 or the front panel 44 forming the input section to control the setting contents of the plurality of peripheral apparatuses connected to the video processor 4 to be set to appropriate setting conditions according to the type of the endoscope 2I connected to the video processor 4.

Note that, in FIG. 16, the monitor, the VTR 7, the printer 8, and the network apparatus 9 are shown as the peripheral apparatuses connected to the peripheral-apparatus control circuit 46. However, the light source apparatus 3 functioning as the peripheral apparatus not connected to the peripheral-apparatus control circuit 46 and the keyboard 6 forming the input section may be included in the peripheral apparatuses and displayed.

Recommended setting items in items that can be set and items that cannot be set (setting impossible) may be clearly indicated with respect to the peripheral apparatus (in FIG. 17, the monitor), setting of which is attempted to be changed, in the connected plurality of peripheral apparatuses as shown in FIG. 17.

When the plurality of peripheral apparatuses connected to the video processor 4 includes a peripheral apparatus (represented as a peripheral apparatus F) for which adjustment (setting) by a setting value or a parameter from the video processor 4 is necessary, (for example, the peripheral-apparatus control circuit 46 of) the video processor 4 may include a menu setting section that automatically displays, according to an input of information concerning a type of the peripheral apparatus F from the keyboard 6 or the like forming the input section to the video processor 4, in a wizard format, menu items for which setting is necessary according to the information concerning the type of the peripheral apparatus F.

For example, by designating the peripheral apparatus F, the menu setting section automatically picks up setting items F1, F2, . . . that need to be set in the peripheral apparatus F as shown in FIG. 18 and displays the setting items F1, F2, . . . on a (peripheral apparatus) menu setting screen. Therefore, the user can easily perform setting of setting values and the like necessary for the peripheral apparatus F according to display contents of the menu setting screen.

Note that an embodiment formed by partially combining parts of the embodiments and the like explained above also belongs to the present invention. The present invention includes the following note.

Note 1: The endoscope system according to claim 1, wherein the display section automatically displays, when the endoscope or the peripheral apparatus is connected, a menu of set respective items in a wizard format according to a type of the endoscope or a type of the peripheral apparatus.

Note 2: The endoscope system according to claim 1, wherein the plurality of functions in the endoscope system 1 includes a plurality of functions included in the signal processing apparatus and one or more functions included in the peripheral apparatus.

What is claimed is:

1. An endoscope system comprising:
a signal processing apparatus to which one endoscope among a plurality of types of endoscopes is connected, the signal processing apparatus performing video processing for an output signal of an image pickup device mounted on the connected endoscope;
an endoscope-type detecting section configured to detect a type of the endoscope connected to the signal processing apparatus;
a function setting section configured to set a plurality of functions in the endoscope system including the signal processing apparatus, the endoscope connected to the signal processing apparatus, and one or more peripheral apparatuses connected to the signal processing apparatus;
an input section configured to input, to the function setting section, data including an instruction for changing the setting;
an output section configured to output, to a display section, a list of setting states of the plurality of functions set by the function setting section; and
a recommended-setting-data storing section configured to store, in association with a name of an observation part or a medical department, recommended setting data for setting the plurality of functions respectively to recommended appropriate setting states,
wherein the function setting section sets the signal processing apparatus to a selected one of the setting of the setting states corresponding to the type of the endoscope and a setting recommended by the recommended setting data, according to an input of the name of the observation part or the medical department inputted from the input section, and automatically sets the plurality of functions respectively to appropriate setting states according to the type of the endoscope detected by the endoscope-type detecting section.

2. The endoscope system according to claim 1, further comprising a setting-data storing section configured to store setting data for the function setting section to set the plurality of functions respectively to the appropriate setting states according to the type of the endoscope.

3. The endoscope system according to claim 2, further comprising a second setting-data storing section configured to store second setting data for setting the plurality of functions in the endoscope system respectively to the appropriate setting states without depending on the type of the endoscope.

4. The endoscope system according to claim 1, wherein the input section includes a specific function button and makes it possible to collectively read out, according to operation of the specific function button, setting contents of the setting states for the plurality of functions set by the function setting section.

5. The endoscope system according to claim 1, wherein
the input section includes a specific function button and reads out, according to operation of the specific function button, the plurality of functions and setting contents of the setting states of the plurality of functions set by the function setting section, and
the display section displays the read-out plurality of functions and the setting contents corresponding to the plurality of functions.

6. The endoscope system according to claim 1, wherein the function setting section acquires data related to function setting accumulated in a server of a network apparatus configuring the peripheral apparatuses and makes it possible to use the data for setting of the plurality of functions of the endoscope system.

7. The endoscope system according to claim 2, wherein the setting-data storing section stores, besides first setting data serving as the setting data associated with the type of the endoscope, third setting data serving as the setting data associated with the type of the endoscope and a user name serving as a name of a user who uses the endoscope system.

8. The endoscope system according to claim 7, wherein, when the setting-data storing section stores the third setting data in the user name same as the user name who uses the endoscope system, the function setting section more preferentially uses the third setting data for the setting of the plurality of functions than the first setting data.

9. The endoscope system according to claim 1, wherein the plurality of types of respective endoscopes include data storing sections configured to store information for identifying the respective types and store setting data for setting the plurality of functions respectively to the appropriate setting states according to the types.

10. The endoscope system according to claim 9, wherein
the signal processing apparatus is configured by a first signal processing apparatus or a second signal processing apparatus, at least one function of the first signal processing apparatus and at least one function of the second signal processing apparatus being different from each other, and
the setting data stored by the data storing section includes setting data for the first and second signal processing apparatuses for appropriately setting the plurality of functions according to each of the first and second signal processing apparatuses.

11. The endoscope system according to claim 9, wherein
the peripheral apparatuses include, as a light source apparatus that supplies illumination light to the endoscope connected to the signal processing apparatus, a first light source apparatus or a second light source apparatus, at least characteristics of the first and second light source apparatuses being different from each other, and
the setting data stored by the data storing section includes setting data for the first and second light source apparatuses for appropriately setting the plurality of functions according to each of the first and second light source apparatuses.

12. The endoscope system according to claim 9, wherein
the signal processing apparatus is configured by a first signal processing apparatus or a second signal processing apparatus, at least one function of the first signal processing apparatus and at least one function of the second signal processing apparatus being different from each other,
the peripheral apparatuses include, as a light source apparatus that supplies illumination light to the endoscope connected to the signal processing apparatus, a first light source apparatus or a second light source apparatus, at least characteristics of the first and second light source apparatuses being different from each other,
the setting data stored by the data storing section includes setting data for the first and second signal processing apparatuses for appropriately setting the plurality of functions according to each of the first and second signal processing apparatuses, and
the setting data for the first and second signal processing apparatuses further include setting data for the light source apparatus for appropriately setting the plurality of functions according to each of the first and second light source apparatuses.

* * * * *